US00PP14579P29

(12) United States Plant Patent
van Kesteren

(10) Patent No.: US PP14,579 P2
(45) Date of Patent: Mar. 9, 2004

(54) EUPHORBIA PLANT NAMED 'MINI MARTINI'

(50) Latin Name: *Euphorbia×maritinii*
Varietal Denomination: Mini Martini

(75) Inventor: Marcus Adrianus van Kesteren, Noordwijkerhout (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 10/313,116

(22) Filed: Dec. 6, 2002

(51) Int. Cl.[7] ..... A01H 5/00
(52) U.S. Cl. ..... Plt./302
(58) Field of Search ..... Plt./302

*Primary Examiner*—Bruce R. Campell
*Assistant Examiner*—Annette H Para
(74) *Attorney, Agent, or Firm*—C. A. Whealy

(57) ABSTRACT

A new and distinct cultivar of Euphorbia plant named 'Mini Martini', characterized by its compact and mounded plant habit; freely branching habit; dense and full plant form; freely flowering habit; and green-colored floral bracts and dark purple-colored nectaries.

2 Drawing Sheets

Botanical classification/cultivar designation: *Euphorbia× maritinii* cultivar Mini Martini.

BACKGROUND OF THE INVENTION

The present invention relates to a new and distinct cultivar of Euphorbia, botanically known as *Euphorbia×maritinii* and hereinafter referred to by the cultivar name 'Mini Martini'.

The new Euphorbia is a naturally-occurring whole plant mutation of an unidentified selection of *Euphorbia× maritinii*, not patented. The new Euphorbia was discovered and selected by the Inventor as a single plant in a controlled environment in Noordwijkerhout, The Netherlands.

Asexual reproduction of the new Euphorbia since 2001 by cuttings taken in a controlled environment in Noordwijkerhout, The Netherlands, has shown that the unique features of this new Euphorbia are stable and reproduced true to type in successive generations.

SUMMARY OF THE INVENTION

The cultivar Mini Martini has not been observed under all possible environmental conditions. The phenotype may vary somewhat with variations in environment such as temperature and light intensity without, however, any variance in genotype.

The following traits have been repeatedly observed and are determined to be the unique characteristics of 'Mini Martini'. These characteristics in combination distinguish 'Mini Martini' as a new and distinct cultivar:

1. Compact and mounded plant habit.
2. Freely branching habit; dense and full plant form.
3. Freely flowering habit.
4. Green-colored floral bracts and dark purple-colored nectaries.

Plants of the new Euphorbia are most similar to plants of the parent selection, however plants of the new Euphorbia are more compact than and about half as tall as plants of the parent selection.

BRIEF DESCRIPTION OF THE PHOTOGRAPHS

The accompanying colored photographs illustrate the overall appearance of the new Euphorbia, showing the colors as true as it is reasonably possible to obtain in colored reproductions of this type. Colors in the photographs may differ slightly from the color values cited in the detailed botanical description which accurately describe the colors of the new Euphorbia.

The photograph on the first sheet comprises a side perspective view of a typical flowering plant of 'Mini Martini'. The photographs on the second sheet are close-up views of typical inflorescences of 'Mini Martini'.

DETAILED BOTANICAL DESCRIPTION

Plants used for the aforementioned photographs and the following description were grown in containers in an outdoor nursery and under conditions which closely approximate commercial production in Lisse, The Netherlands. During the production of the plants, day temperatures ranged from 9 to 21° C. and night temperatures ranged from 3 to 11° C. Plants were about two years old when the photographs and description were taken. The photographs and description were taken in May, 2002. In the description, color references are made to The Royal Horticultural Society Colour Chart, 1995 Edition, except where general terms of ordinary dictionary significance are used.

Botanical classification: *Euphorbia maritinii* cultivar Mini Martini.

Parentage: Naturally-occurring whole plant mutation of an unidentified selection of *Euphorbia maritinii, not patented.*

Propagation:

*Type.*—By cuttings.

*Time to initiate roots.*—About 14 days at temperatures of 14° C.

*Time to develop roots.*—About 40 days at temperatures of 21° C.

*Root description.*—Fine, well-branched.

Plant description:

*Plant form and growth habit.*—Compact and mounded plant habit; inverted triangle; perennial subshrub. Moderate growth rate. Appropriate for 9 to 13-cm containers.

*Branching habit.*—Freely branching, usually about 55 lateral branches develop per plant; dense and bushy plant form.

*Plant height.*—About 40 cm.

*Plant diameter.*—About 45 cm.

*Lateral branch description* (*peduncles*).—Length: About 30 cm. Diameter: About 4 mm. Internode length: About 2 cm. Strength: Strong. Texture: Smooth, glabrous. Color: Young stems, 144C; older stems, 187C.

Foliage description:

*Arrangement.*—Alternate, simple; symmetrical; sessile.

*Length.*—About 5.7 cm.

*Width.*—About 9 mm.

*Shape.*—Oblanceolate.

*Apex.*—Acute.

*Base.*—Cuneate.

*Margin.*—Entire.

*Texture, upper surface.*—Glabrous; smooth.

*Texture, lower surface.*—Pubescent.

*Color.*—Young foliage, upper surface: 141A to 141B. Young foliage, lower surface: 138A. Mature foliage, upper surface: 137B. Mature foliage, lower surface: 138B. Venation, upper and lower surfaces: 145A to 145B.

Flower description:

*Natural flowering season.*—Late April through late May in Lisse, The Netherlands; flowering continuous during this period.

*Flower arrangement.*—Single rotate flowers arranged in umbel-like compound terminal cymes. Very freely flowering with about 120 flower buds and flowers per inflorescence. Flowers face upright and outwardly. Flowers self-cleaning and not fragrant.

*Inflorescence height.*—About 13 cm.

*Inflorescence diameter.*—About 9.5 cm.

*Flower diameter.*—About 1.2 cm.

*Flower depth* (*height*).—About 5 mm.

*Flower longevity on the plant.*—About four weeks.

*Flower buds.*—Length: About 2 mm. Diameter: About 2 mm. Shape: Broadly elliptic. Color: 144C.

*Floral bracts.*—Quantity/arrangement: Two; opposite. Length: About 7 mm. Width: About 1.2 cm. Shape: Orbicular. Apex: Rounded. Base: Fused. Margin: Entire. Texture, upper and lower surfaces: Glabrous; smooth. Color: When opening, upper and lower surfaces: 144B to 144C. Fully opened, upper and lower surfaces: 144B to 144A.

*Pedicels.*—Length: About 2.5 mm. Diameter: Less than 1.5 mm. Angle: Erect to about 50° from vertical. Strength: Moderate. Texture: Smooth, glabrous. Color: 144B.

*Reproductive organs.*—Androecium: No male flowers observed. Gynoecium: Pistil number per flower: One, three-carpelled. Pistil length: About 3 mm. Style length: About 2 mm. Style color: 144C. Stigma shape: Cleft. Stigma color: 151A.

*Nectaries.*—Quantity per flower: About four. Shape: Lunate. Length: About 1.5 mm. Width: About 2.5 mm. Color: 187A becoming closer to 184A to 184B with development.

*Fruit/seed.*—Fruit and seed production has not been observed.

Disease/pest resistance: Plants of the new Euphorbia have not been observed to be resistant to pathogens and pests common to Euphorbia.

Temperature tolerance: Plants of the new Euphorbia are tolerant to temperatures as low as −10° C. and as high as 35° C.

It is claimed:

1. A new and distinct Euphorbia plant named 'Mini Martini', as illustrated and described.

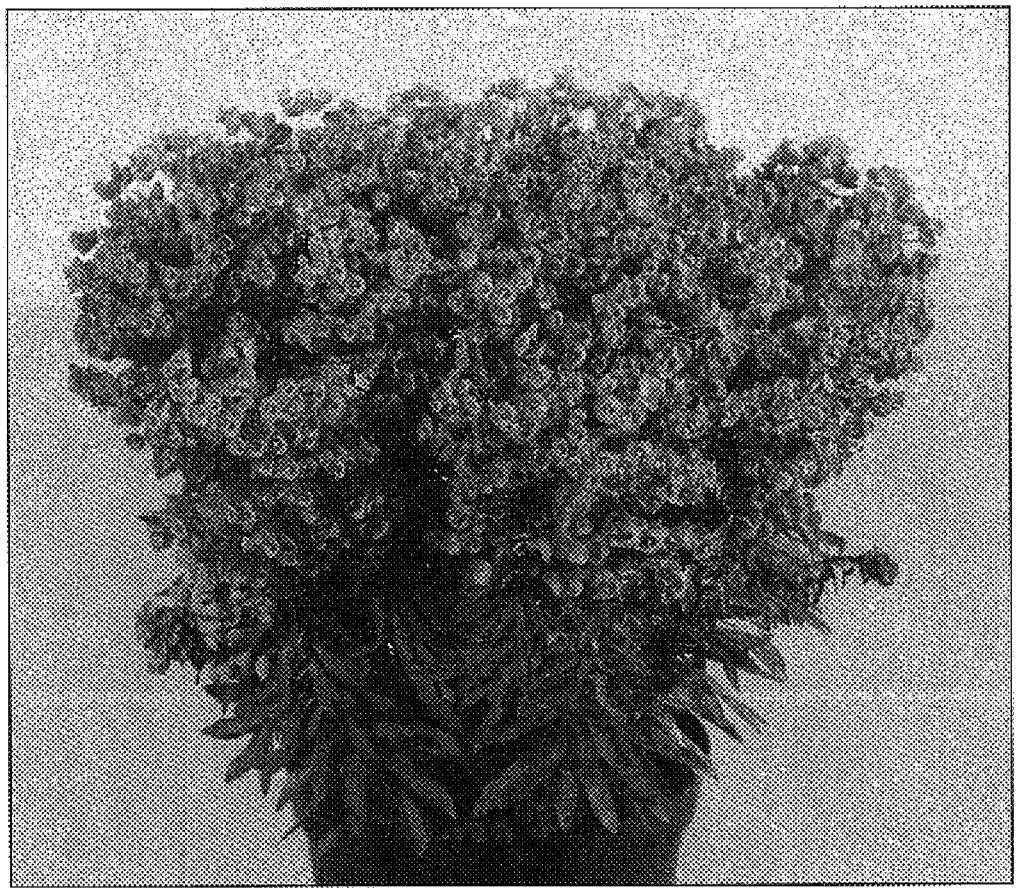

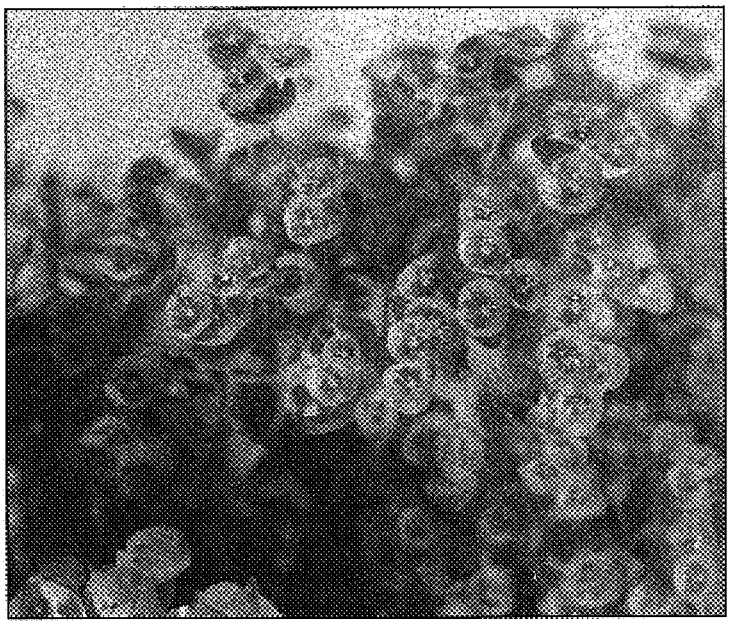
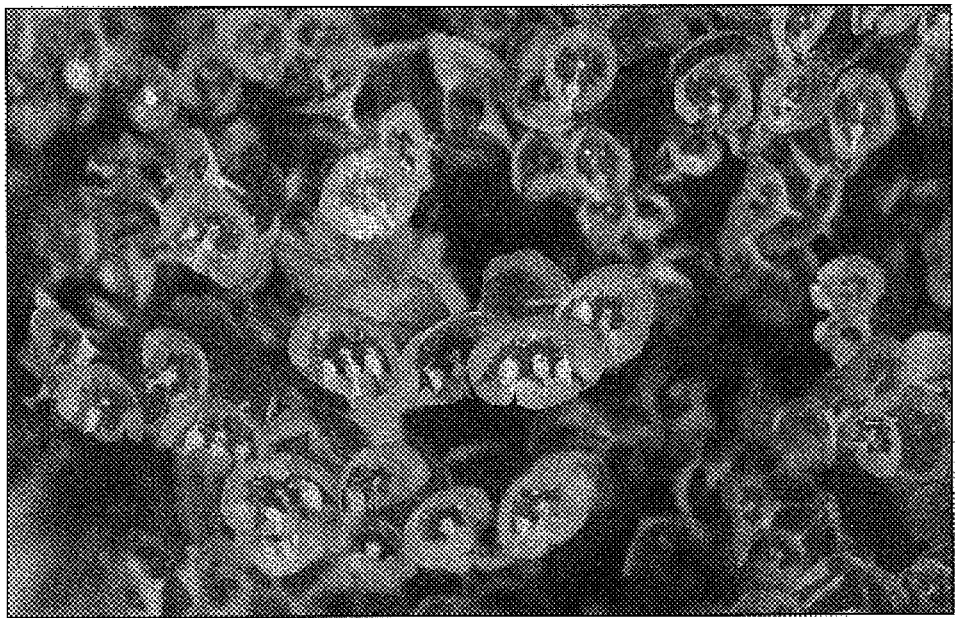

* * * * *